US010583289B2

(12) United States Patent
Mishra et al.

(10) Patent No.: US 10,583,289 B2
(45) Date of Patent: *Mar. 10, 2020

(54) COCHLEAR IMPLANT SYSTEM INCLUDING AN IMPLANTABLE BATTERY (71) Applicant: ADVANCED BIONICS AG, Staefa (CH)

(72) Inventors: Lakshmi N. Mishra, Carlsbad, CA (US); Lee F. Hartley, Carlsbad, CA (US)

(73) Assignee: Advanced Bionics AG, Staefa (CH)

( * ) Notice: Subject to any disclaimer, the term of this patent is extended or adjusted under 35 U.S.C. 154(b) by 75 days.

This patent is subject to a terminal disclaimer.

(21) Appl. No.: 15/857,589

(22) Filed: Dec. 28, 2017

(65) Prior Publication Data

US 2018/0117327 A1 May 3, 2018

Related U.S. Application Data

(63) Continuation of application No. 14/411,482, filed as application No. PCT/US2012/044850 on Jun. 29, 2012, now Pat. No. 9,889,300.

(51) Int. Cl.
*A61N 1/36* (2006.01)
*A61N 1/378* (2006.01)

(52) U.S. Cl.
CPC ......... *A61N 1/36036* (2017.08); *A61N 1/378* (2013.01); *A61N 1/3787* (2013.01)

(58) Field of Classification Search
CPC .................................................. A61N 1/3787
See application file for complete search history.

(56) References Cited

U.S. PATENT DOCUMENTS 6,445,162 B1    9/2002  Mukainakano
6,894,456 B2    5/2005  Tsukamoto et al.
(Continued)

FOREIGN PATENT DOCUMENTS

WO    2010/028436    3/2010

OTHER PUBLICATIONS

Final Office Action received in U.S. Appl. No. 14/411,482 dated Aug. 21, 2017.

(Continued)

*Primary Examiner* — Carl H Layno
*Assistant Examiner* — Jennifer L Ghand
(74) *Attorney, Agent, or Firm* — ALG Intellectual Property, LLC (57) ABSTRACT

An exemplary cochlear implant system for a patient includes a cochlear implant, a sound processor, and an implantable battery configured to be implanted within the patient. The cochlear implant is configured to 1) determine that a signal is not being provided to the cochlear implant by a device external to the patient, 2) determine, in response to the determination that the signal is not being provided to the cochlear implant, that an amount of power remaining in the implantable battery is above a predetermined threshold amount, and 3) initiate, in response to the determination that the amount of power remaining in the implantable battery is above the predetermined threshold, an idle mode in which the cochlear implant remains powered on while waiting for one or more signals to be provided to the cochlear implant by the device external to the patient.

20 Claims, 6 Drawing Sheets

(56) References Cited

U.S. PATENT DOCUMENTS

| | | | |
|---|---|---|---|
| 7,003,353 | B1 | 2/2006 | Parkhouse |
| 7,346,397 | B2 | 3/2008 | Money et al. |
| 7,529,587 | B2 | 5/2009 | Single |
| 8,280,522 | B2 | 10/2012 | Zierhofer et al. |
| 8,611,995 | B2 | 12/2013 | Van Hulle et al. |
| 9,192,772 | B1 | 11/2015 | Tsukamoto et al. |
| 9,889,300 | B2 * | 2/2018 | Mishra ............... A61N 1/3787 |
| 2002/0076071 | A1 | 6/2002 | Single |
| 2005/0037256 | A1 | 2/2005 | Mukainakano |
| 2008/0009918 | A1 | 1/2008 | Zierhofer et al. |
| 2008/0123882 | A1 | 5/2008 | Bauml et al. |
| 2008/0174278 | A1 | 7/2008 | Masias et al. |
| 2011/0112608 | A1 | 5/2011 | Zierhofer |
| 2012/0041515 | A1 | 2/2012 | Meskens et al. |
| 2012/0150259 | A1 | 6/2012 | Meskens |

OTHER PUBLICATIONS

International Search Report and Written Opinion received in International Application No. PCT/US12/044850, dated Jul. 4, 2013.

Non-Final Office Action received in U.S. Appl. No. 14/411,482 dated Mar. 13, 2017.

Briggs, Robert J. et al., "Future technology in cochlear implants: assessing the benefit," Cochlear Implants International, 2011, vol. 12, No. S1, pp. S22-S25, Department of Otolarygology, University of Melbourne, East Melbourne, Australia.

Briggs, Robert J. et al., "Initial Clinical Experience With a Totally Implantable Cochlear Implant Research Device," Otology & Neurotology, vol. 29, No. 2, 2008, pp. 114-119, The University of Melbourne Department of Otolaryngology, Sydney, Australia.

* cited by examiner

COCHLEAR IMPLANT SYSTEM INCLUDING AN IMPLANTABLE BATTERY

RELATED APPLICATIONS

The present application is a continuation application of U.S. patent application Ser. No. 14/411,482, filed Dec. 26, 2014 and issued as U.S. Pat. No. 9,889,300, which application is a U.S. National Stage Entry of PCT Application No. PCT/US12/44850, filed Jun. 29, 2012. The contents of these applications are incorporated herein by reference in their respective entireties.

BACKGROUND INFORMATION

Conventional cochlear implant systems include a sound processor configured to be located external to a patient (e.g., behind the ear) and a cochlear implant configured to be implanted within the patient. In this configuration, the sound processor may process audio signals presented to the patient and wirelessly transmit stimulation parameters to the cochlear implant so that the cochlear implant may generate and apply electrical stimulation representative of the audio signals to the patient.

An externally located sound processor is typically further configured to wirelessly transmit operating power to the cochlear implant. To this end, a battery may be attached to the sound processor and used to provide the power that is wirelessly transmitted to the cochlear implant. Unfortunately, wireless transmission of power between an externally located sound processor and an implanted cochlear implant is relatively inefficient. Hence, a relatively large battery is required to provide a reasonable amount of battery life for the cochlear implant. As a result, the unit that houses the battery and the sound processor and that has to be worn or otherwise carried by the patient is relatively large, bulky, and aesthetically unpleasing.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

A cochlear implant system that includes an implantable battery is described herein. As will be described in more detail below, the cochlear implant system may include 1) a cochlear implant configured to be implanted within a patient, 2) a sound processor configured to be located external to the patient and to direct the cochlear implant to apply electrical stimulation representative of one or more audio signals to the patient, and 3) an implantable battery configured to be implanted within the patient and to provide operating power for the cochlear implant.

By providing operating power for a cochlear implant with a battery that is also implanted within a patient (as opposed to with a battery located external to the patient), various benefits may be achieved. For example, the size of the battery may be significantly reduced by avoiding the inefficiencies involved in wireless transmission of power to the cochlear implant. Moreover, the need for the patient to always wear or carry an externally located battery (e.g., a battery connected to the sound processor) may be obviated, thereby significantly reducing the size and weight of the external components that the user has to wear or carry. This, in turn, may make the cochlear implant system less visible and more aesthetically pleasing to the patient.

Figure 1:
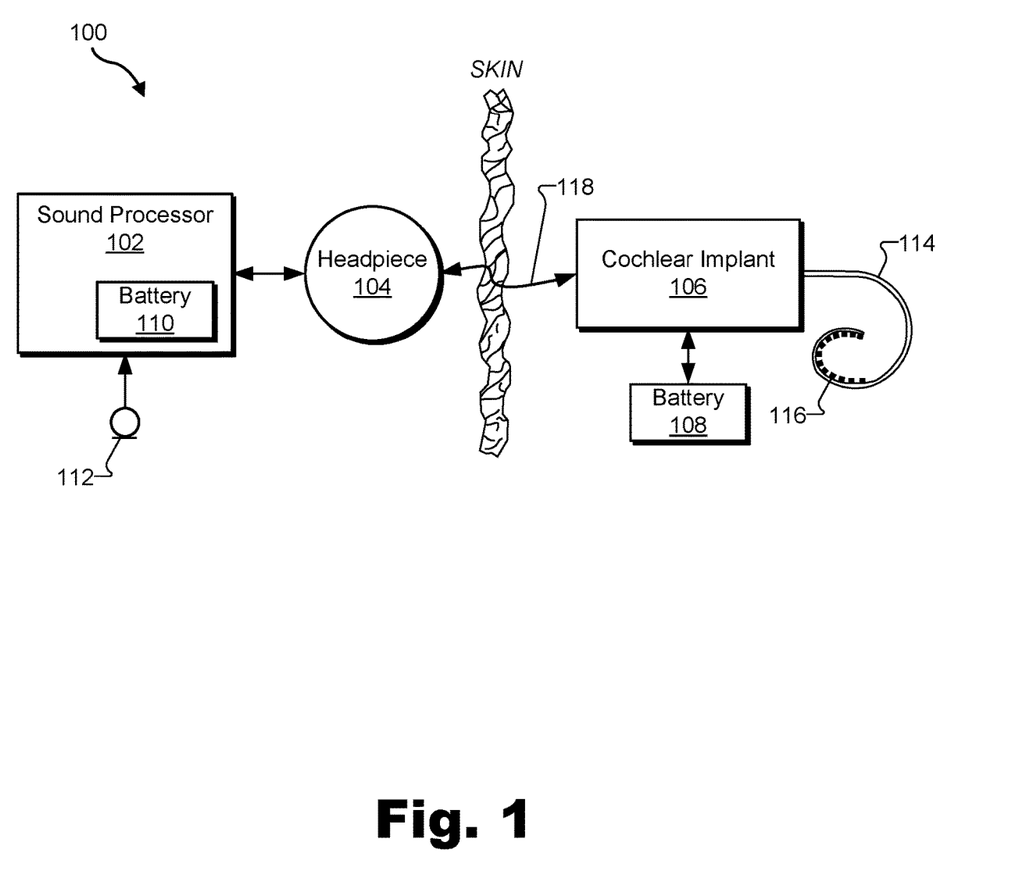
FIG. 1 illustrates an exemplary cochlear implant system according to principles described herein.

FIG. 1 illustrates an exemplary cochlear implant system 100. Cochlear implant system 100 may include a sound processor 102, a headpiece 104, a cochlear implant 106, an implantable battery 108, an external battery 110, a microphone 112, and a lead 114 having a plurality of electrodes 116 disposed thereon. As shown in FIG. 1, sound processor 102, headpiece 104, external battery 110, and microphone 112 may be located external to a cochlear implant patient. Cochlear implant 106, implantable battery 108, lead 114, and electrodes 116 may be implanted within the patient. As will be described in more detail below, additional or alternative components may be included within cochlear implant system 100 as may serve a particular implementation.

Sound processor 102 is configured to direct cochlear implant 106 to generate and apply electrical stimulation (also referred to herein as "stimulation current") representative of one or more audio signals (e.g., one or more audio signals detected by microphone 112, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 102 may process the one or more audio signals in accordance with a selected sound processing strategy or program to generate appropriate stimulation parameters for controlling cochlear implant 106. Sound processor 102 may include or be implemented by a behind-the-ear ("BTE") unit, a body worn device, a portable speech processor ("PSP"), an electro-acoustic stimulation ("EAS") device, and/or any other sound processing unit as may serve a particular implementation.

In some examples, sound processor 102 may wirelessly transmit stimulation parameters and/or power signals to cochlear implant 106 by way of a wireless communication link 118 between headpiece 104 and cochlear implant 106. It will be understood that communication link 118 may include a bi-directional communication link and/or one or more dedicated uni-directional communication links.

Headpiece 104 may be communicatively coupled to sound processor 102 and may include one or more interface components configured to facilitate selective wireless coupling of sound processor 102 to cochlear implant 106. Headpiece 104 may be additionally or alternatively be used to selectively and wirelessly couple any other external device to cochlear implant 106. To this end, headpiece 104 may be configured to be affixed to the patient's head and positioned such that a coil housed within headpiece 104 is communicatively coupled to a corresponding coil included within or otherwise associated with cochlear implant 106. In this manner, stimulation parameters and power signals may be wirelessly transmitted between sound processor 102 and cochlear implant 106 via communication link 118.

Cochlear implant 106 may include any type of implantable stimulator that may be used in association with the systems and methods described herein. For example, cochlear implant 106 may include an implantable cochlear stimulator. In some alternative implementations, cochlear implant 106 may include a brainstem implant and/or any other type of cochlear implant that may be implanted within a patient and configured to apply stimulation to one or more stimulation sites located along an auditory pathway of a patient.

In some examples, cochlear implant 106 may be configured to generate electrical stimulation representative of an audio signal processed by sound processor 102 (e.g., an audio signal detected by microphone 112) in accordance with one or more stimulation parameters transmitted thereto by sound processor 102. Cochlear implant 106 may be further configured to apply the electrical stimulation to one or more stimulation sites within the patient via one or more electrodes 116 disposed along lead 114. In some examples, cochlear implant 106 may include a plurality of independent current sources each associated with a channel defined by one or more of electrodes 116. In this manner, different stimulation current levels may be applied to multiple stimulation sites simultaneously by way of multiple electrodes 116. In such examples, cochlear implant system 100 may be referred to as a "multi-channel cochlear implant system."

As shown, cochlear implant system 100 may include an implantable battery 108 and, optionally, an external battery 110 configured to be located external to the patient. External battery 110 may be communicatively coupled to (e.g., included within) sound processor 102 and configured to provide operating power for sound processor 102. Implantable battery 108 may be communicatively coupled to cochlear implant 106 (e.g., by way of one or more wires) and configured to provide operating power for cochlear implant 106. In some examples, implantable battery 108 exclusively provides (i.e., is the sole source of) operating power for cochlear implant 106, regardless of whether sound processor 102 or any other external device is wirelessly coupled to cochlear implant 106.

In some examples, implantable battery 108 is rechargeable. For example, sound processor 102 may charge implantable battery 108 using power provided by external battery 110. To illustrate, sound processor 102 may generate one or more power signals that include power provided by external battery 110 and transmit the one or more power signals to cochlear implant 106 by way of headpiece 104. Additionally or alternatively, as will be described below, implantable battery 108 may be charged using a charging device or other type of device configured to be located external to the patient.

Figure 2:
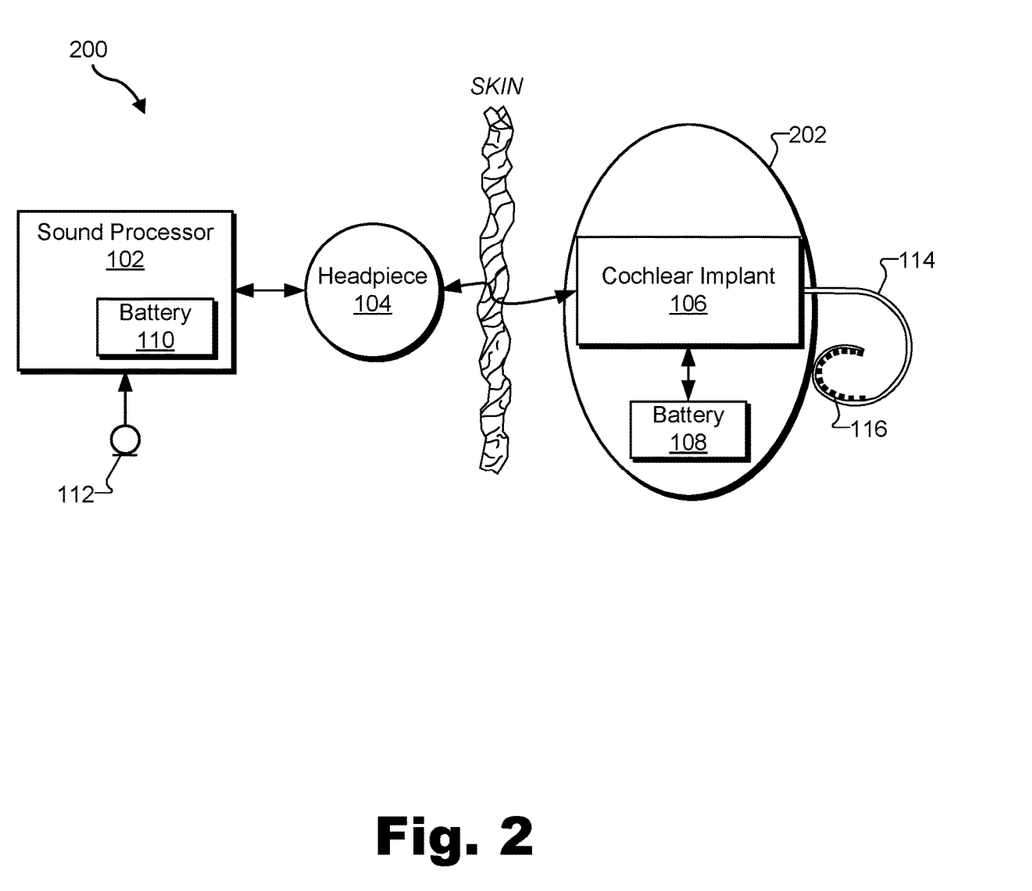
FIG. 2 shows an exemplary configuration of the system of FIG. 1 in which the implantable battery and the cochlear implant are housed within an overmold according to principles described herein.

Implantable battery 108 may be implanted within the patient in any suitable manner. For example, FIG. 2 shows an exemplary configuration 200 of system 100 in which implantable battery 108 and cochlear implant 106 are housed within an overmold 202, which may be implanted within the patient in any suitable manner. Overmold 202 may be made out of any suitable material as may serve a particular implementation.

Figure 3:
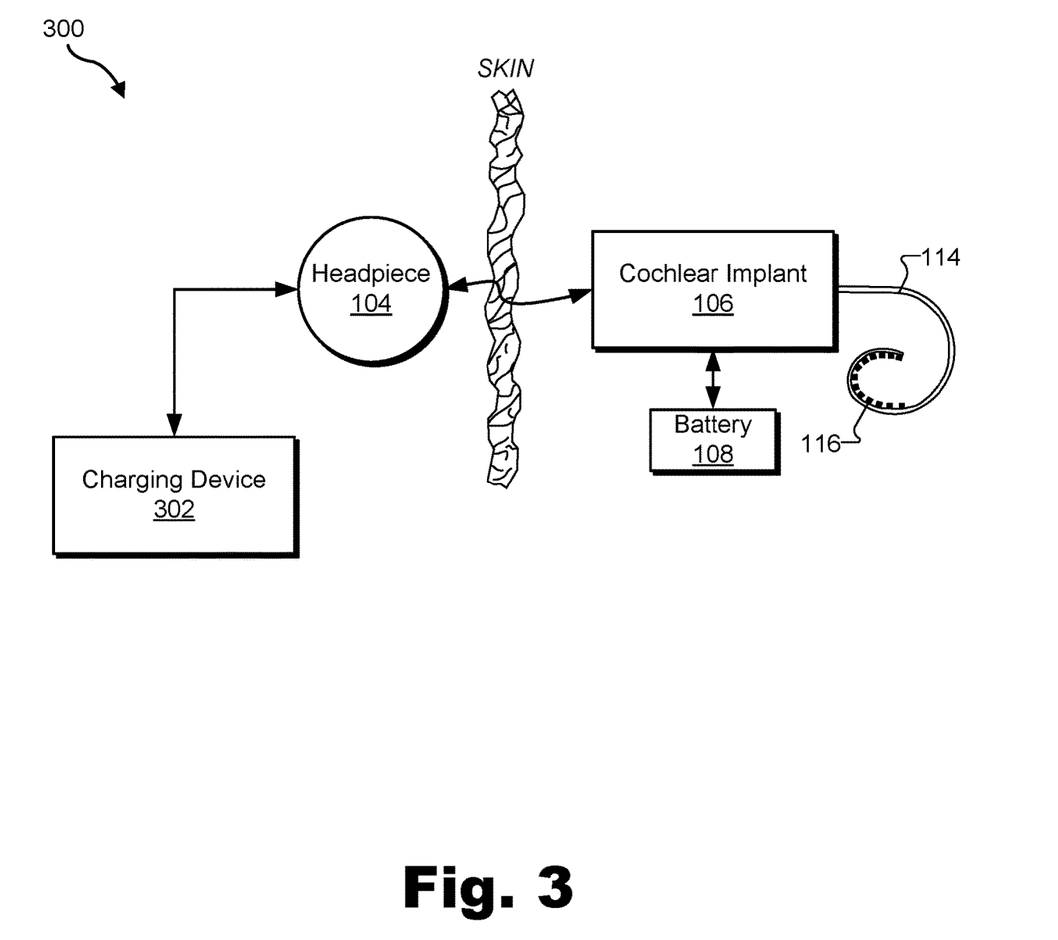
FIG. 3 shows an exemplary configuration wherein a charging device is wirelessly coupled to a cochlear implant by way of a headpiece according to principles described herein.

As mentioned, one or more other external devices may be wirelessly coupled to cochlear implant 106 by way of headpiece 104. For example, FIG. 3 shows an exemplary configuration 300 wherein a charging device 302 is wirelessly coupled to cochlear implant 106 by way of headpiece 104. Charging device 302 may include any suitable device configured to charge battery 108 (e.g., by transmitting one or more power signals to cochlear implant 106 by way of headpiece 104). It will be recognized that charging device 302 is merely illustrative of the many different external devices that may be wirelessly coupled to cochlear implant 106 by way of headpiece 104.

Figure 4:
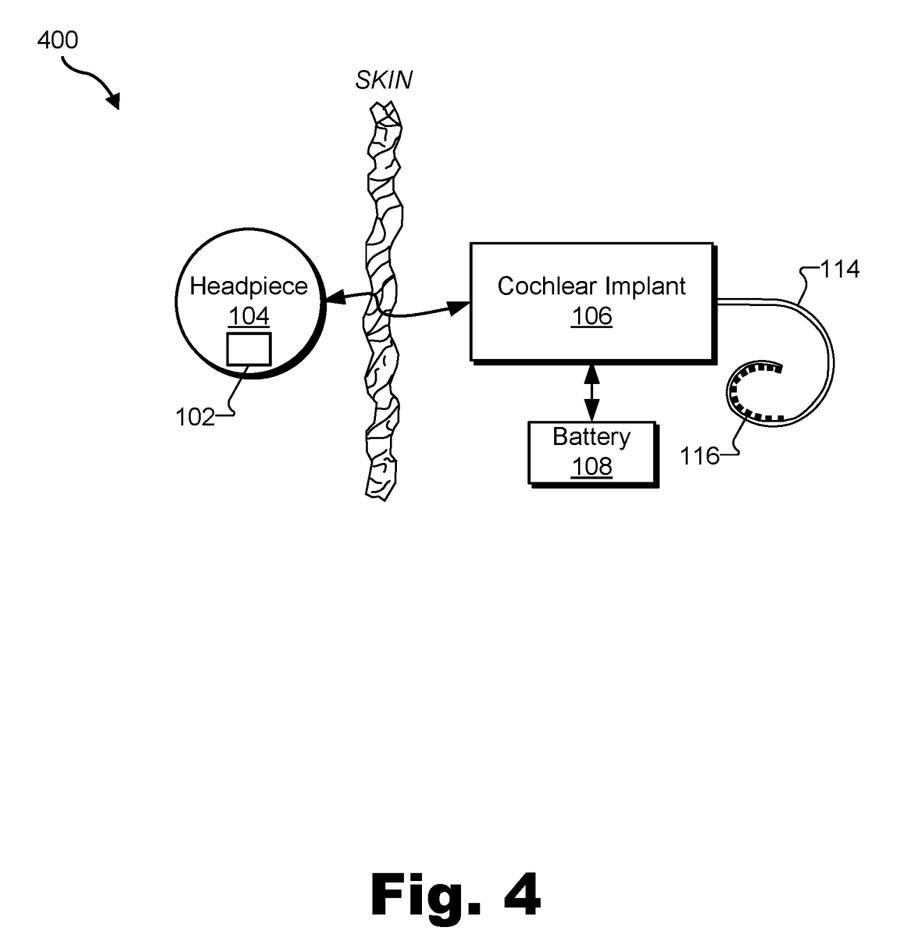
FIG. 4 shows an exemplary one piece system that may be realized in accordance with the methods and systems described herein.

In some examples, the reduced power requirements that result from battery 108 being implanted within the patient may facilitate use of a one piece system ("OPS"). As used herein, a "one piece system" refers to a cochlear implant system in which the sound processor is housed within headpiece 104. To illustrate, FIG. 4 shows an exemplary one piece system 400 that may be realized in accordance with the methods and systems described herein. As shown, sound processor 102 is housed within headpiece 104. System 100 may obviate the need for the patient to wear anything behind his or her ear, which may be desirable for a variety of reasons.

Figure 5:
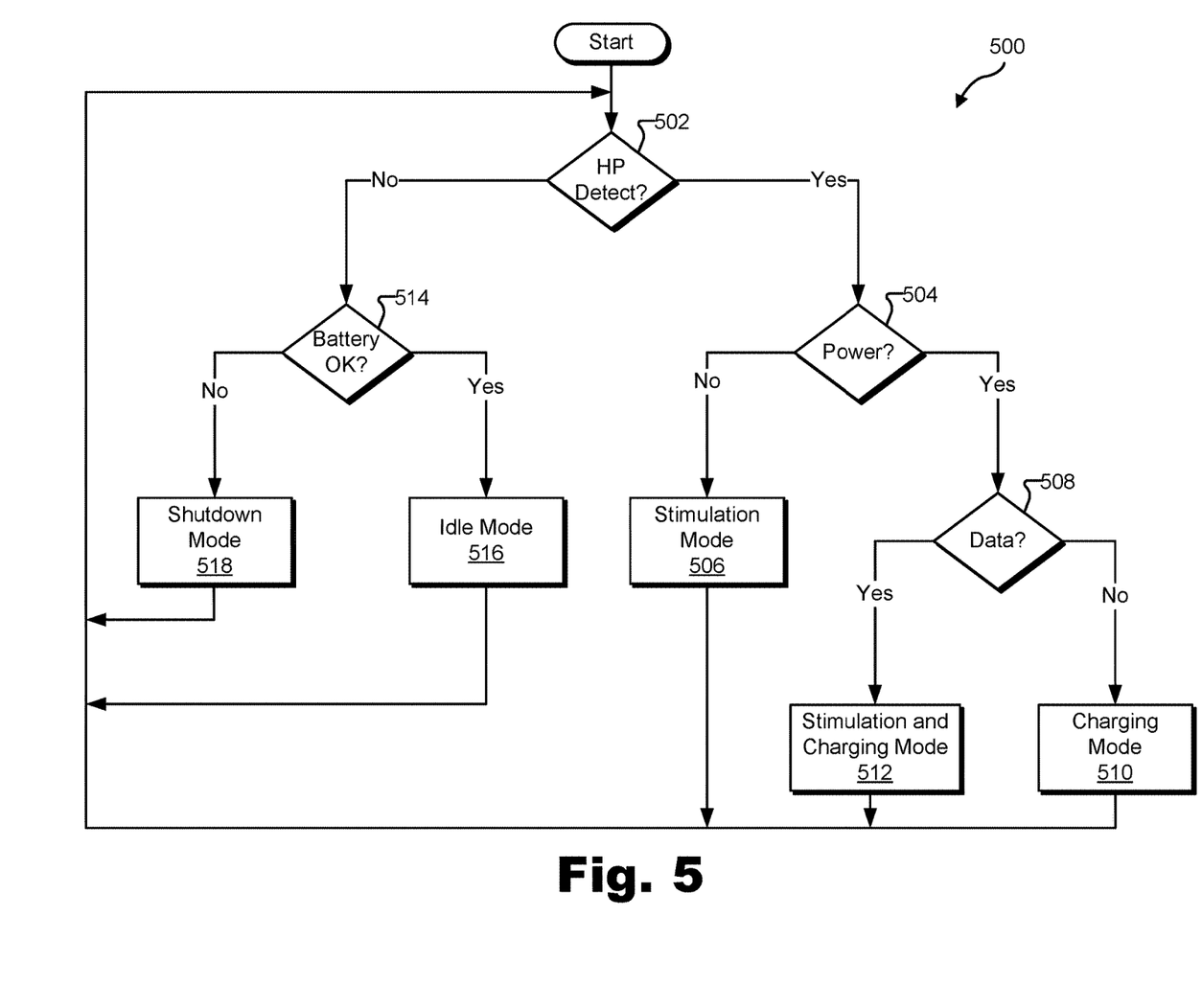
FIG. 5 is an exemplary flow chart that illustrates an exemplary operation of a cochlear implant according to principles described herein.

FIG. 5 is an exemplary flow chart 500 that illustrates an exemplary operation of cochlear implant 106. While FIG. 5 illustrates exemplary steps according to one embodiment, other embodiments may omit, add to, reorder, and/or modify any of the steps shown in FIG. 5.

In decision block 502, cochlear implant 106 determines whether a signal is being provided (e.g., transmitted) by way of headpiece 104. This may be performed in any suitable manner. For example, cochlear implant 106 may continuously, periodically, and/or intermittently monitor for or otherwise attempt to detect a signal being transmitted by way of headpiece 104. In some examples, the signal is generated or otherwise provided by sound processor 102. Alternatively, the signal may be generated or otherwise provided by charging device 302 or any other suitable external device as may serve a particular implementation.

If a signal is being provided by way of headpiece 104 (Yes; decision block 502), cochlear implant 106 determines whether a power level of the signal exceeds a predetermined threshold level (decision block 504). If the power level of the signal does not exceed the predetermined threshold level (No; decision block 504), cochlear implant 106 may determine that the signal is not configured to be used to charge implantable battery 108 and may therefore initiate a stimulation mode in which cochlear implant 106 applies electrical stimulation to the patient in accordance with one or more stimulation parameters represented by the signal (step 506) without charging implantable battery 108 at the same time.

However, if the power level of the signal does exceed the predetermined threshold level (Yes; decision block 504), cochlear implant 106 determines whether the signal also includes data representative of one or more stimulation parameters (decision block 508). If the signal does not include data representative of one or more stimulation parameters (No; decision block 508), cochlear implant 106 initiates a charging mode in which the signal is used to charge implantable battery 108 (step 510). If the signal does include data representative of one or more stimulation parameters (Yes; decision block 508), cochlear implant 106 initiates both the charging mode and the stimulation mode in which the signal is used to charge implantable battery 108 while cochlear implant 106 applies electrical stimulation to the patient in accordance with the one or more stimulation parameters (step 512).

Returning to decision block 502, if cochlear implant 106 determines that a signal is not being provided by headpiece 104 (No; decision block 502), cochlear implant 106 may determine whether an amount of power remaining in implantable battery 108 is above a predetermined threshold amount (decision block 514). If cochlear implant 106 determines that the amount of power remaining in implantable battery 108 is above a predetermined threshold amount (Yes; decision block 514), cochlear implant 106 initiates an idle mode in which cochlear implant 106 remains powered on while waiting for one or more signals to be provided by way of headpiece 104 (step 516). However, If cochlear implant 106 determines that the amount of power remaining in implantable battery 108 is below the predetermined threshold amount (No; decision block 514), cochlear implant 106 initiates a shutdown mode in which cochlear implant 106 at least partially shuts down while waiting for one or more signals to be provided by way of headpiece 104. While in shutdown mode, cochlear implant 106 may wake up (i.e., power on) on a periodic basis in order to monitor for one or more signals possibly being provided by way of headpiece 104.

Figure 6:
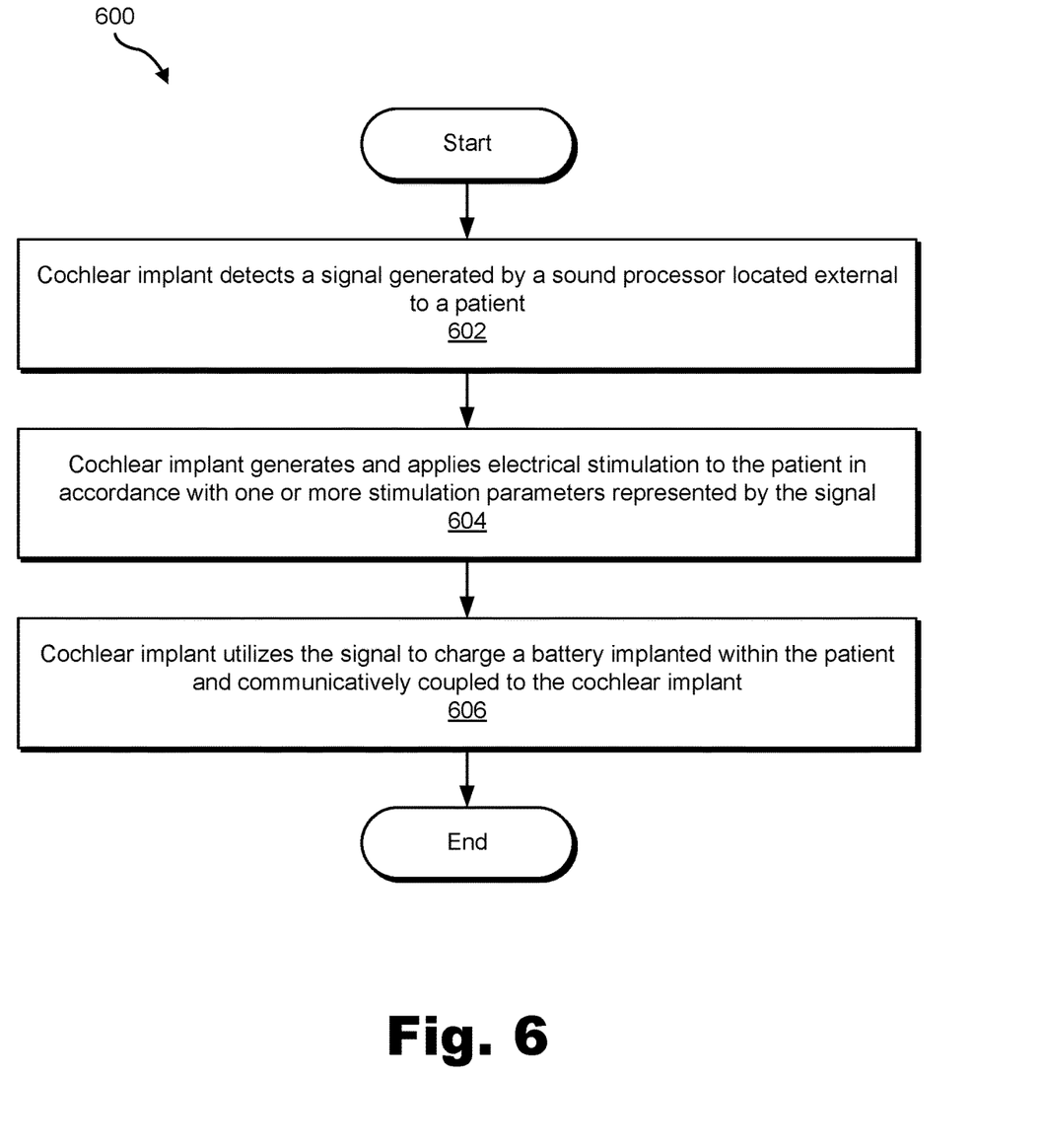
FIG. 6 illustrates an exemplary cochlear implant operation method according to principles described herein.

FIG. 6 illustrates an exemplary cochlear implant operation method 600. While FIG. 6 illustrates exemplary steps according to one embodiment, other embodiments may omit, add to, reorder, and/or modify any of the steps shown in FIG. 6. One or more of the steps shown in FIG. 6 may be performed by any component or combination of components of cochlear implant 106.

In step 602, a cochlear implant detects a signal generated by a sound processor located external to a patient. Step 602 may be performed in any of the ways described herein.

In step 604, the cochlear implant generates and applies electrical stimulation to the patient in accordance with one or more stimulation parameters represented by the signal. Step 604 may be performed in any of the ways described herein.

In step 606, the cochlear implant utilizes the signal to charge a battery implanted within the patient and communicatively coupled to the cochlear implant. As described above, the implanted battery may exclusively provide operating power to the cochlear implant regardless of whether a sound processor or any other external device is wirelessly coupled to the cochlear implant. Step 606 may be performed in any of the ways described herein.

In some examples, an external device (e.g., a sound processor 102) may transmit a signal to cochlear implant 106 that instructs the cochlear implant to utilize power provided by external battery 110 in place of or in addition to power provided by implantable battery 108. For example, cochlear implant 106 may initially power up using power provided by implanted battery 108. Cochlear implant 106 may then detect a signal provided by sound processor 102 that includes an instruction to use power provided by implanted battery 108. After a certain amount of time, sound processor 102 may transmit another signal to cochlear implant 106 that directs cochlear implant 106 to switch to using power provided by external battery 110. In this manner, the source of power utilized by cochlear implant 106 may be dynamically managed in order to conserve battery life of implantable battery 108.

In some examples, an exemplary cochlear implant system may include 1) a cochlear implant configured to be implanted within a patient, 2) an implantable battery communicatively coupled to the cochlear implant and configured to be implanted within the patient and to provide operating power for the cochlear implant, and 3) a headpiece configured to be located external to the patient and to be wirelessly coupled to the sound processor, the headpiece comprising one or more interface components configured to facilitate selective wireless coupling of one or more external devices to the cochlear implant. As described above, the implantable battery may exclusively provide operating power for the cochlear implant while the one or more external devices are wirelessly coupled to the cochlear implant.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   a cochlear implant configured to be implanted within a patient;
   a sound processor configured to be located external to the patient and to direct the cochlear implant to apply electrical stimulation representative of one or more audio signals to the patient; and
   an implantable battery configured to be implanted within the patient and to provide operating power for the cochlear implant;
   wherein the cochlear implant is further configured to:
      determine that a signal is not being provided to the cochlear implant by a device other than the sound processor and external to the patient;
      determine, in response to the determination that the signal is not being provided to the cochlear implant, that an amount of power remaining in the implantable battery is above a predetermined threshold amount; and
      initiate, in response to the determination that the amount of power remaining in the implantable battery is above the predetermined threshold, an idle mode in which the cochlear implant remains powered on while waiting for one or more signals to be provided to the cochlear implant by the device external to the patient.

2. The system of claim 1, further comprising an overmold configured to house both the cochlear implant and the implantable battery.

3. The system of claim 1, further comprising an external battery configured to be communicatively coupled to the sound processor and to be located external to the patient, wherein the external battery is configured to provide operating power for the sound processor.

4. The system of claim 3, wherein the sound processor is further configured to charge the implantable battery using power provided by the external battery.

5. The system of claim 3, wherein the cochlear implant is configured to:
   initially use operating power provided by the implantable battery;
   receive, from the sound processor, an instruction to switch from using the operating power provided by the implantable battery to using operating power provided by the external battery; and switch, in response to the instruction, from using the operating power provided by the implantable battery to using the operating power provided by the external battery.

6. The system of claim 1, wherein the implantable battery is communicatively coupled to the cochlear implant by way of one or more wires.

7. The system of claim 1 wherein the implantable battery exclusively provides the operating power for the cochlear implant.

8. The system of claim 1, wherein the cochlear implant is further configured to:
   detect another signal being provided to the cochlear implant by the device external to the patient;
   determine that a power level of the another signal exceeds a predetermined threshold level; and
   initiate, in response to the determination that the power level of the another signal exceeds the predetermined threshold level, a charging mode in which the another signal is used to charge the implantable battery.

9. The system of claim 8, wherein the cochlear implant is further configured to:
   determine that the another signal comprises data representative of one or more stimulation parameters; and
   initiate, in response to the determination that the another signal comprises data representative of one or more stimulation parameters, a stimulation mode in which the cochlear implant applies electrical stimulation to the patient in accordance with the one or more stimulation parameters.

10. A system comprising:
    a cochlear implant configured to be implanted within a patient;
    a sound processor configured to be located external to the patient and to direct the cochlear implant to apply electrical stimulation representative of one or more audio signals to the patient; and
    an implantable battery configured to be implanted within the patient and to provide operating power for the cochlear implant;
    wherein the cochlear implant is further configured to:
      determine that a signal is not being provided to the cochlear implant by a device other than the sound processor and external to the patient;
      determine, in response to the determination that the signal is not being provided to the cochlear implant, that an amount of power remaining in the implantable battery is below a predetermined threshold amount; and
      initiate, in response to the determination that the amount of power remaining in the implantable battery is below the predetermined threshold, a shutdown mode in which the cochlear implant at least partially shuts down while waiting for one or more signals to be provided to the cochlear implant by the device external to the patient.

11. The system of claim 10, wherein the cochlear implant is further configured to at least periodically monitor for the one or more signals while the cochlear implant is operating in the shutdown mode.

12. The system of claim 10, further comprising an overmold configured to house both the cochlear implant and the implantable battery.

13. The system of claim 10, further comprising an external battery configured to be communicatively coupled to the sound processor and to be located external to the patient, wherein the external battery is configured to provide operating power for the sound processor.

14. The system of claim 13, wherein the sound processor is further configured to charge the implantable battery using power provided by the external battery.

15. The system of claim 10, wherein the implantable battery is communicatively coupled to the cochlear implant by way of one or more wires.

16. The system of claim 10, wherein the implantable battery exclusively provides the operating power for the cochlear implant.

17. The system of claim 10, wherein the cochlear implant is further configured to:
    detect another signal being provided to the cochlear implant by the device external to the patient;
    determine that a power level of the another signal exceeds a predetermined threshold level; and
    initiate, in response to the determination that the power level of the another signal exceeds the predetermined threshold level, a charging mode in which the another signal is used to charge the implantable battery.

18. The system of claim 17, wherein the cochlear implant is further configured to:
    determine that the another signal comprises data representative of one or more stimulation parameters; and
    initiate, in response to the determination that the another signal comprises data representative of one or more stimulation parameters, a stimulation mode in which the cochlear implant applies electrical stimulation to the patient in accordance with the one or more stimulation parameters.

19. The system of claim 17, wherein the implantable battery is configured to provide operating power for the cochlear implant while the implantable battery is being charged by the another signal.

20. A method comprising:
    determining, by a cochlear implant that is implanted within a patient, that a signal generated by a device external to the patient is not being provided to the cochlear implant;
    determining, by the cochlear implant in response to the determining that the signal is not being provided to the cochlear implant, that an amount of power remaining in an implantable battery implanted within the patient and configured to provide operating power for the cochlear implant is above a predetermined threshold amount; and
    initiating, by the cochlear implant in response to the determining that the amount of power remaining in the implantable battery is above the predetermined threshold, an idle mode in which the cochlear implant remains powered on while waiting for one or more signals to be provided to the cochlear implant by the device external to the patient.

* * * * *